(12) United States Patent
Borden

(10) Patent No.: US 6,254,561 B1
(45) Date of Patent: Jul. 3, 2001

(54) METHOD AND APPARATUS FOR POSITIONING A PATIENT FOR RADIATION THERAPY

(75) Inventor: Carla K. Borden, Jonesboro, AR (US)

(73) Assignee: Diversified Marketing Association, Inc., Lynchburg, VA (US)

( * ) Notice: Subject to any disclaimer, the term of this patent is extended or adjusted under 35 U.S.C. 154(b) by 0 days.

(21) Appl. No.: 09/365,881

(22) Filed: Aug. 3, 1999

Related U.S. Application Data

(60) Provisional application No. 60/096,181, filed on Aug. 11, 1998.

(51) Int. Cl.[7] .................................................. A61F 5/00
(52) U.S. Cl. ............................. 602/24; 128/845; 128/882
(58) Field of Search ................................. 128/845, 846, 128/882; 602/23, 24, 27, 28, 32, 36

(56) References Cited

U.S. PATENT DOCUMENTS

| | | |
|---|---|---|
| 1,047,457 * | 12/1912 | Steimer ............................. 128/888 |
| 1,230,512 | 6/1917 | Poehner . |
| 1,845,338 | 2/1932 | Querna . |
| 2,815,021 | 12/1957 | Freeman . |
| 2,895,471 * | 7/1959 | Rollie .................................. 128/888 |
| 3,776,540 * | 12/1973 | Comando ............................ 128/882 |
| 4,046,143 | 9/1977 | Bell ..................................... 128/133 |
| 4,576,151 | 3/1986 | Carmichael .......................... 128/80 |
| 4,608,971 * | 9/1986 | Borschneck ............................ 602/23 |
| 4,691,698 | 9/1987 | Bremer ................................. 128/80 |
| 5,311,366 | 5/1994 | Gerace ................................ 359/879 |
| 5,362,305 | 11/1994 | Varn ..................................... 602/24 |
| 5,558,628 | 9/1996 | Bzoch ................................... 602/24 |
| 5,681,270 | 10/1997 | Klearman et al. .................... 602/24 |

* cited by examiner

*Primary Examiner*—Michael A. Brown
(74) *Attorney, Agent, or Firm*—Millen, White, Zelano & Branigan, P.C.

(57) ABSTRACT

The method and apparatus for positioning a patient for radiation therapy includes a stabilization bar placed between the legs and secured to the legs of a patient to hold the legs in the frogleg position. The frogleg position is attained by positioning the patient in the supine position, then drawing the feet of the patient up as much as possible. The patient then abducts their thighs. The feet of the patient are then strapped together and the stabilization bar positioned between the patient's legs.

1 Claim, 3 Drawing Sheets

METHOD AND APPARATUS FOR POSITIONING A PATIENT FOR RADIATION THERAPY

This application claims the benefit of the filing date of U.S. Provisional Application Ser. No 60/096,181, filed Aug. 11, 1998.

The present invention generally relates to radiation therapy and more particularly to a method and apparatus for positioning a patient for radiation therapy, particularly radiation therapy of a patient in a "frogleg" position.

BACKGROUND OF THE PRESENT INVENTION

It is well known in the art of radiation therapy to position a patient in the "frogleg" position for radiation therapy to be performed at the pelvic region. In the frogleg position, the patient lies on his back with his/her legs bent at the knees and spread apart and with the bottoms of the feet touching each other. This frogleg position is characterized also by the raised knees. This position is so beneficial in radiation therapy, because it decreases the amount of skin folds at or near the treatment field and places as much of the femur as possible out of the treatment area. One of the problems in positioning a patient in the frogleg position is that it is difficult to obtain a consistent frogleg position from the patient because the legs must be held spread apart while being bent at the knees and with the feet touching each other. Another problem is that it is difficult to stabilize the patient in the desired position throughout the duration of the radiation therapy treatment. Finally, repeatability is important in radiation therapy where multiple treatments are common. It is difficult to position a patient in a repeatable position over multiple radiation treatments.

Several prior art references teach abduction devices that may be fitted on patients with various orthopedic conditions. See U.S. Pat. Nos. 5,558,628; 5,362,305 and 1,230,512. Devices for accomplishing simple leg abduction, however, are not acceptable in creating the frogleg position for radiation therapy. The knees must also be elevated to be most effective in radiation therapy.

OBJECT OF THE PRESENT INVENTION

An object of the present invention is to overcome the above problems and provide a novel method and apparatus for positioning a patient in the frogleg position for radiation therapy at the pelvic region or other regions associated with the legs and hips.

A further object of the present invention is to provide a novel method and apparatus which can be used to consistently reproduce the same frogleg position and which moreover will stabilize the position throughout the duration of the radiation therapy.

A further object of the present invention is to provide a novel method and apparatus that will achieve the foregoing objects and yet may be economically manufactured and implemented for use in radiation therapy practice.

SUMMARY OF THE INVENTION

In accordance with the present invention, a patient is first placed in a supine position, and is then asked to flex the hips and bend the knees and draw the feet up as much as possible. The next step is that the patient abducts the thighs and turns the feet inward to brace the soles of the feet against each other. The next step is that the feet are strapped together. Finally, a stabilizing strut such as a stabilizing bar is placed between the legs at the femoral, patella junction, to thus maintain the legs apart and then the strut is fastened such as by straps to hold the desired position. Radiation therapy may then be conducted upon the patient in conventional fashion during which the patient is always positioned in the desired frogleg position.

IN THE DRAWINGS

DETAILED DESCRIPTION OF THE PREFERRED EMBODIMENT

Figure 1:
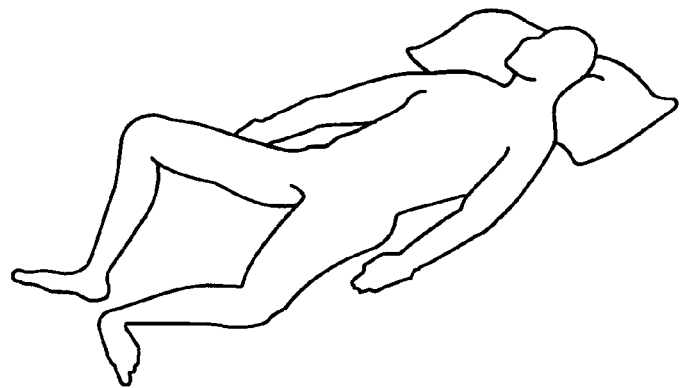
FIG. 1 is a diagrammatic view of a patient shown in the frogleg position.
Figure 2:
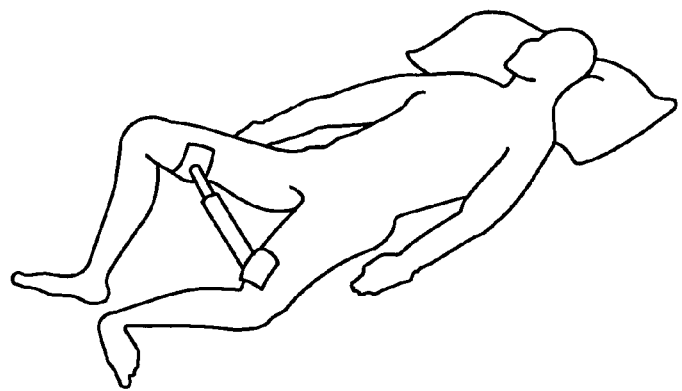
FIG. 2 is a view similar to FIG. 1 but showing the patient with a stabilizing strut secured between the patient's legs.
Figure 3:
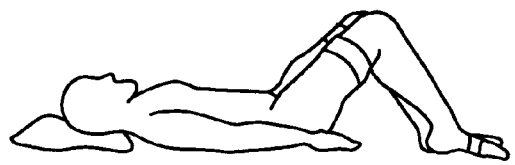
FIG. 3 is a side elevational view of the patient in the frogleg position.
Figure 4:
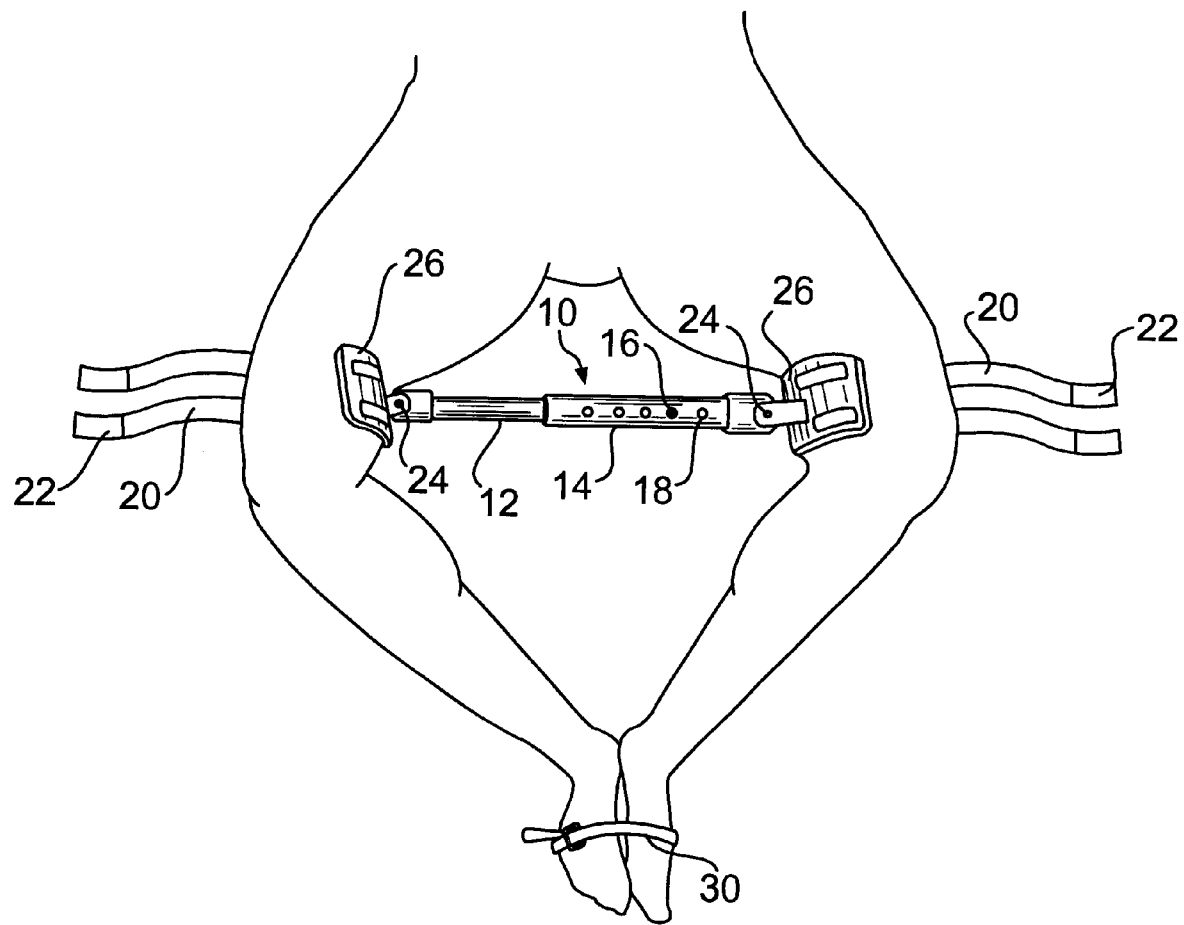
FIG. 4 is a top view showing only a portion of the patient to an enlarged scale.

Referring now to the drawings in detail, FIG. 1 shows a patient in the "frogleg" position which is used for conducting radiation therapy at the pelvic region. In that position the legs are bent at the knees with the thighs spread apart and the bottoms of the feet touching each other. A stabilization strut preferably a bar 10 made of any suitable material is placed between the knees and secured to the legs to hold the patient in the desired frogleg position shown in FIGS. 2, 3 and 4. In the preferred embodiment the stabilization bar 10 includes two telescoping pieces 12 and 14, one being slidably within the other and the pieces being made from any suitable material such as aluminum or any other light weight material including plastic. Once the telescoping bars are properly positioned at the desired length, a locking device such as a pin 16 and slot 18 connection shown in FIG. 4 is employed to hold the tubes in the adjusted position. The ends of the bar 10 are preferably connected to hinges 24 that are connected to C-shaped cuffs 26. Once stabilization bar 10 is secured between the legs of the patient, it is then fastened to the legs in any suitable manner such as for example straps 20 having Velcro fasteners 22 that are connected to the cuffs 26. The straps 20 wrap around the legs and are fastened by the Velcro fasteners 22.

The method of the present invention for placing and holding the patient in the "frogleg" position is to first place the patient in a supine position. Then have the patient flex the hips and knees and draw the feet up as much as possible as shown in FIGS. 3 and 4. The next step is to have the patient abduct the thighs and turn the feet inward to brace the soles of the feet against each other. Next the feet are strapped together as shown in FIGS. 3 and 4 at 30. The stabilization bar 10 is then placed between the legs at the femoral, patella junction and adjusted in length and then locked by insertion of pin 16 in one of the slots 18. Finally, the stabilization bar 10 is secured to the patients legs which in the preferred embodiment is accomplished by the Velcro straps 22 which engage around the legs to hold the bar in the desired position.

Figure 5:
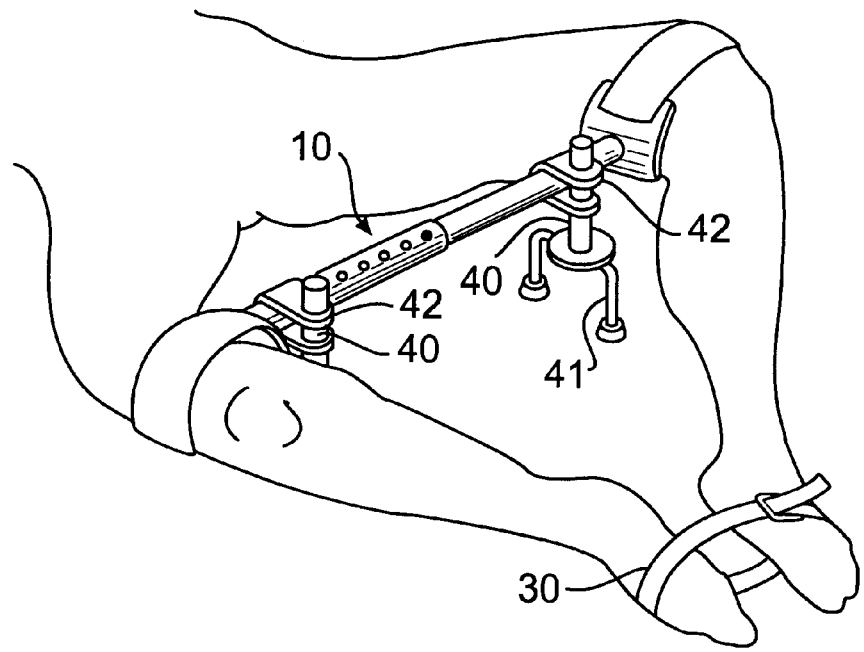
FIG. 5 is a perspective view similar to FIG. 4 but showing the patient with an alternative embodiment of a stabilization strut secured between the patient's leg.

FIG. 5 illustrates a further embodiment of the stabilization bar 10. Support frames 40 are attached to the bar 10 to further support the legs of the patient in the frogleg position. The legs 41 of the frame 40 may or may not be removably attached to the radiation treatment table on which the patient is lying. Further, the clamps 42 which connect the frames 40 to the bar 10 are adjustable so that the height of the bar 10 from the treatment table (not shown) can be adjusted. By attaching the frames 40 to a treatment table and then adjusting the height of the bar 10 to a specific height, radiation therapy for a given patient may be accurately reproduced. This is particularly effective when the stabilization bar 10 is set at a predetermined distance for a given patient. In this way, the patient is comfortably held in the same frogleg position for each radiation treatment that he/she receives.

Figure 6:
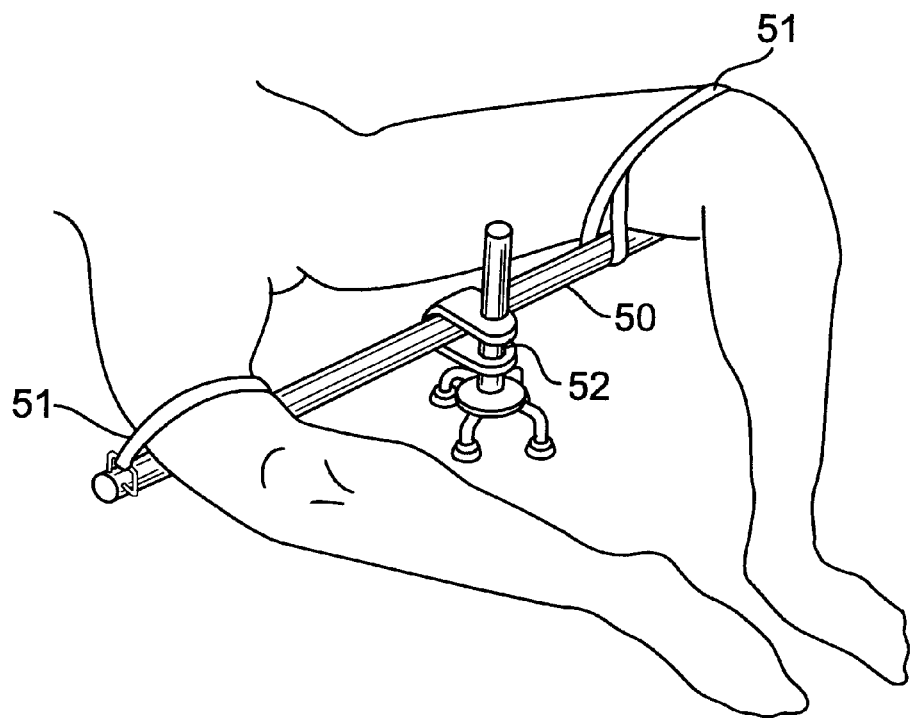
FIG. 6 is a perspective view of still a further embodiment of a patient with a stabilizing strut secured between the patient's legs.

FIG. 6 depicts a further embodiment of the present invention. A support bar 50 having straps 51 attached a either end is supported by a second frame 52. In use, a patient merely drapes his/her legs over the bar 50 as shown. The straps are then attached around the leg of the patient and pulled to a predetermined distance from the end of the support bar 50. Alternatively, the support bar 50 may be a telescoping bar whereby the bar can be adjusted to predetermined length through other means as, for instance, shown in earlier embodiments described herein. In this embodiment, as in the one described in FIG. 5, the height of the support bar 50 may be adjusted so that the specific frogleg position of a patient may be exactly reproduced over a number of treatments. The embodiment shown in FIG. 6 has a single support frame 52. Like the embodiment shown in FIG. 5, there may be one or more support frames depending on the specific needs of a therapy or the table on which the patient lies.

The invention has been shown and described above in connection with preferred embodiments, and it is understood that many modifications, substitutions and additions may be made which are within the spirit and scope of the invention and the following claims.

What is claimed is:

1. A method for positioning a patient for radiation therapy comprising:

placing a patient in a supine position on a treatment surface;

drawing the feet of the patient up;

directing the patient to abduct their thighs;

strapping the feet of the patient together;

placing a stabilization strut between the patient's legs;

adjusting the length of the strut and then locking it; and securing the ends of the strut to the patient's legs whereby the legs are maintained in the frog leg position.

* * * * *